(12) United States Patent
Nelson

(10) Patent No.: US 10,960,147 B2
(45) Date of Patent: Mar. 30, 2021

(54) FLEX NEEDLE

(71) Applicant: FLEXTRONICS AP, LLC, San Jose, CA (US)

(72) Inventor: Andrew P. Nelson, Dallas, TX (US)

(73) Assignee: Flextronics AP, LLC, San Jose, CA (US)

(*) Notice: Subject to any disclaimer, the term of this patent is extended or adjusted under 35 U.S.C. 154(b) by 317 days.

(21) Appl. No.: 15/958,042

(22) Filed: Apr. 20, 2018

(65) Prior Publication Data
US 2019/0321562 A1 Oct. 24, 2019

(51) Int. Cl.
*A61M 5/32* (2006.01)
*A61M 5/158* (2006.01)

(52) U.S. Cl.
CPC ............ *A61M 5/329* (2013.01); *A61M 5/158* (2013.01); *A61M 5/3286* (2013.01); *A61M 2205/0216* (2013.01)

(58) Field of Classification Search
CPC .... A61M 5/329; A61M 5/158; A61M 5/3286; A61M 2205/0216; A61M 2025/0063
See application file for complete search history.

(56) References Cited

U.S. PATENT DOCUMENTS

| 5,330,441 | A | 7/1994 | Prasad et al. | |
|---|---|---|---|---|
| 2004/0133124 | A1* | 7/2004 | Bates | A61B 10/0275 600/564 |
| 2010/0121307 | A1* | 5/2010 | Lockard | A61M 37/0015 604/506 |
| 2010/0152663 | A1 | 6/2010 | Darr | |
| 2011/0313357 | A1* | 12/2011 | Skutnik | A61M 5/46 604/151 |
| 2013/0035609 | A1* | 2/2013 | Darr | A61M 25/0138 600/567 |
| 2014/0357983 | A1* | 12/2014 | Toomey | A61B 17/3478 600/424 |
| 2015/0351959 | A1* | 12/2015 | Clem | A61M 25/0662 604/521 |
| 2016/0317220 | A1* | 11/2016 | Guo | A61M 25/005 |
| 2016/0361047 | A1* | 12/2016 | Rohl | A61L 31/022 |
| 2017/0120010 | A1 | 5/2017 | Burkholz et al. | |

(Continued)

FOREIGN PATENT DOCUMENTS

WO 2018/226515 A1 12/2018

OTHER PUBLICATIONS

International Search Report for WO Application PCT/US2019/028370 dated Aug. 13, 2019.

*Primary Examiner* — Jenna Zhang
(74) *Attorney, Agent, or Firm* — Volpe Koenig

(57) ABSTRACT

A flexible medical needle for extended indwelling periods is provided. The medical needle apparatus includes a spine body and a flexible shaft portion. The spine body has a length between a first end, comprising a piercing tip, and a second end. The flexible shaft portion may be disposed on at least a portion of the spine body, forming a needle shaft having a passage along a portion of the length of the spine body. The spine body may also be coiled forming an axial passage within the spine body. In this latter embodiment, the flexible shaft portion surrounds the spine body. In each embodiment, the spine body is configured to facilitate bending, allowing for the medical needle to remain indwelling with reduced discomfort.

8 Claims, 6 Drawing Sheets

(56) References Cited

U.S. PATENT DOCUMENTS

2017/0234411 A1\*  8/2017  Dewaele .............. F16H 19/005
                                                74/479.01
2017/0258988 A1\*  9/2017  Meyer ................... A61M 5/168

\* cited by examiner

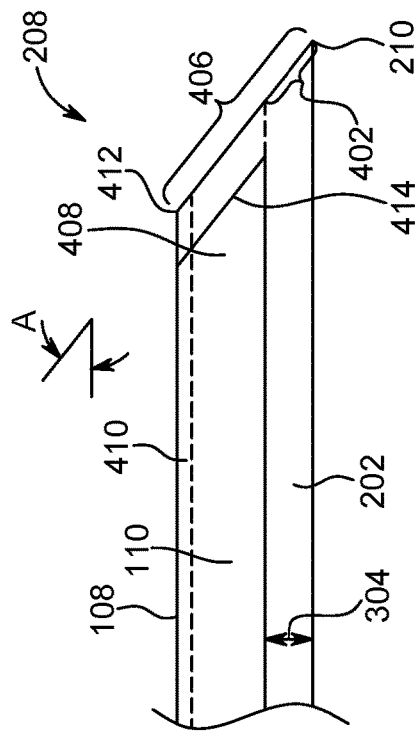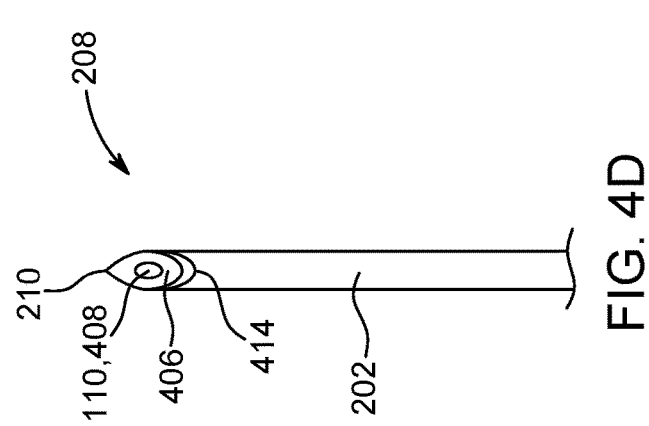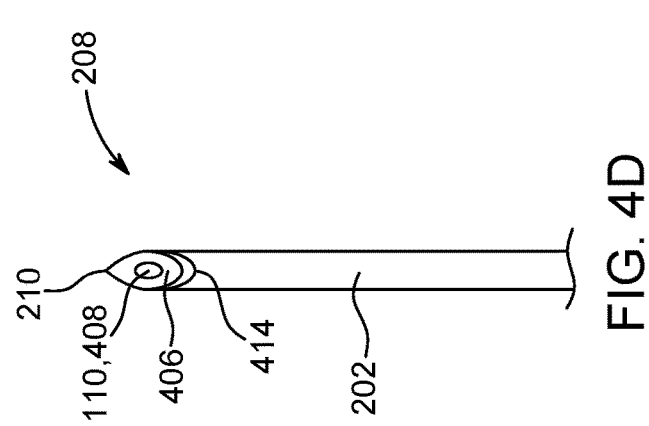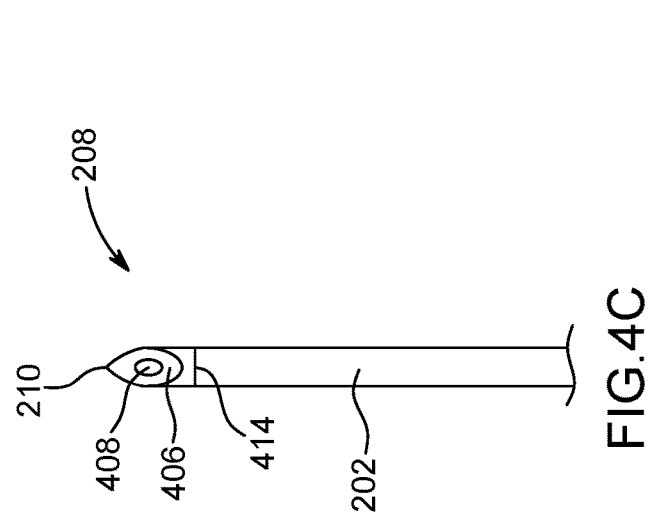

FLEX NEEDLE

FIELD OF INVENTION

Embodiments of the present disclosure generally relate to medical apparatuses, for example medical needles, and in particular, needles with increased flexibility in at least one plane.

BACKGROUND

Medical needles are typically rigid metal tubes with a piercing end for piercing the skin and penetrating into the tissue below the skin. In some applications, it is desirable to have the needle remain in the tissue (i.e., indwelling) for an extended period of time. Under those conditions, it is often necessary to immobilize the site to aid patient comfort by preventing movement between the tissue and the rigid needle. This is not always convenient or desirable.

In some known indwelling applications, a needle is first used to pierce the skin and penetrate into the tissue. A flexible tube placed over the needle as a sheath to follow the needle to a site within the tissue. Once the tube reaches a desired location, the needle is removed from the tube, leaving the flexible tube in the tissue (i.e. a cannula). However, this is a multi-step process to place a flexible tube in tissue.

Accordingly, a need exists for a flexible needle that can be easily placed in tissue without the need for a separate flexible tube to be place over the needle, and that can remain indwelling for an extended period of time without patient discomfort.

SUMMARY

Embodiments of flexible medical needle for extended indwelling periods are provided herein. The flexible medical needle apparatus comprises a spine body and a flexible shaft portion. The spine body has a length between a first end having a piercing tip, and a second end. The flexible shaft portion has a proximal end and a distal end adjacent to the first and second ends of the spine body, respectively. The flexible shaft portion may be disposed on at least a portion of the spine body forming a needle shaft comprising a passage along at least a portion of the length of the spine body. The spine body may also be coiled forming an axial passage along the length of the spine body. In this latter embodiment, the flexible shaft portion surrounds the spine body.

Other and further embodiments of the present invention are described below.

BRIEF DESCRIPTION OF THE DRAWINGS

Embodiments of the present invention, briefly summarized above and discussed in greater detail below, can be understood by reference to the illustrative embodiments of the invention depicted in the appended drawings. It is to be noted, however, that the appended drawings illustrate only typical embodiments of this invention and are therefore not to be considered limiting of its scope, for the invention may admit to other equally effective embodiments.

FIGS. 4A and 4C are side and top views, respectively, of a piercing tip in accordance with an embodiment.

FIGS. 4B and 4D are side and top views, respectively, of a piercing tip in accordance with an embodiment.

Figure 1:
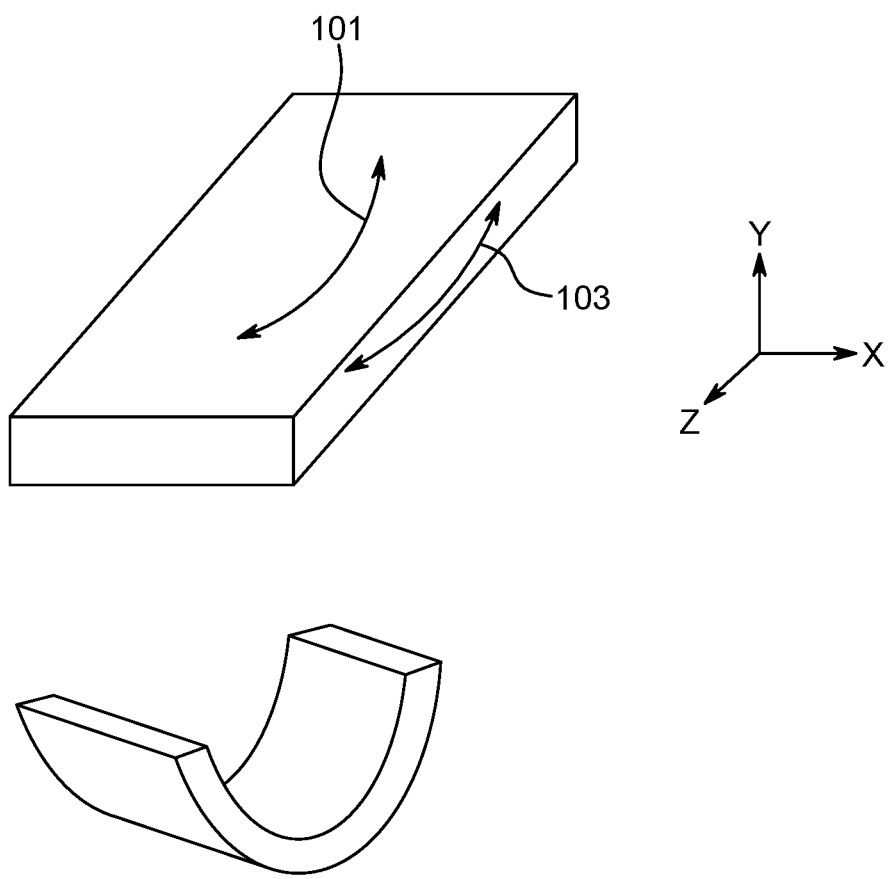
FIG. 1 is a perspective view representing bending of a known rectangular element.

To facilitate understanding, identical reference numerals have been used, where possible, to designate identical elements that are common in the figures. The figures are not drawn to scale and may be simplified for clarity. It is contemplated that elements and features of one embodiment may be beneficially incorporated in other embodiments without further recitation.

While described in reference to a medical needle, the present invention may be modified for a variety of applications employing a cannula while remaining within the spirit and scope of the claimed invention, since the range of the potential applications is great, and because it is intended that the present invention be adaptable to many such variations.

DETAILED DESCRIPTION

Certain terminology is used in the following description for convenience only and is not limiting. The words "top" and "bottom" designate directions in the drawings to which reference is made. The word "interiorly" refers to the orientation along the longitudinal axis of the apparatus that is further from the surface of the ends of the apparatus. The word "radial" refers to directions radially towards or away from an axis of the part being referenced. "Axially" refers to a direction along the axis of a shaft or other part. "Longitudinal" refers to spanning the length, or part of the length, of the shaft or other part. A reference to a list of items that are cited as "at least one of a, b, or c" (where a, b, and c represent the items being listed) means any single one of the items a, b, or c, or combinations thereof. The terminology includes the words specifically noted above, derivatives thereof and words of similar import.

It is generally understood that an element with a rectangular-like cross section has enhanced flexibility in the direction of the smaller dimension. For example, the element illustrated in FIG. 1 has enhanced flexibility (i.e., bends more easily) in the direction indicated by curve 103 (bending in the YZ plane) than in the direction indicated by curve 101 (bending in the XZ plane).

Figure 2A:
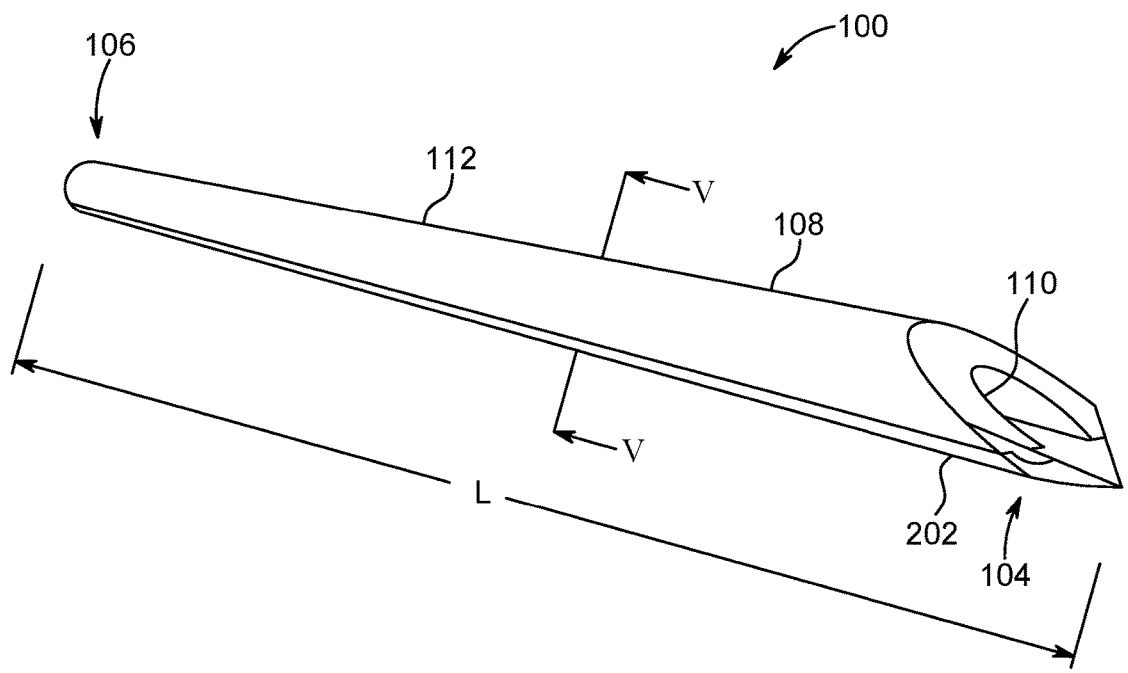
FIG. 2A is a perspective view of a needle in accordance with an embodiment of the present disclosure.

FIG. 2A depicts a needle 100 in accordance with a non-limiting embodiment of the present invention. The needle 100 includes a spine body 202 with a flexible shaft portion 108 disposed on top. The spine body 202 and the flexible shaft portion 108 define an axial passage 110 formed at least partially along an interior portion of the length L. The first end 104 is adapted to pierce the skin and penetrate into tissue below. The second end 106 may be adapted for connection to a medical apparatus to supply a material to the axial passage 110 or to facilitate removal of material through the axial passage 110.

Non-limiting examples of the flexible material may include Teflon, silicon, polytetrafluoroethylene-based polymers, a thermoplastic elastomer (TPE), or other polymeric material having a low durometer. In an embodiment, the flexible material is biocompatible, although non-biocompatible materials may be used if bio-compatibility is not required for example. In an embodiment, the flexible material is a polymer, although non-polymeric materials may be used if the material is flexible. In a preferred embodiment, the material used to form the flexible portion has a lubricity characteristic to facilitate insertion of the needle 100. The lubricity may be a feature of the flexible material itself, or that of an additive to the material or a coating applied to the external surfaces of the flexible shaft portion 108. In an embodiment the flexible material could be any material that could stretch.

Figure 2B:
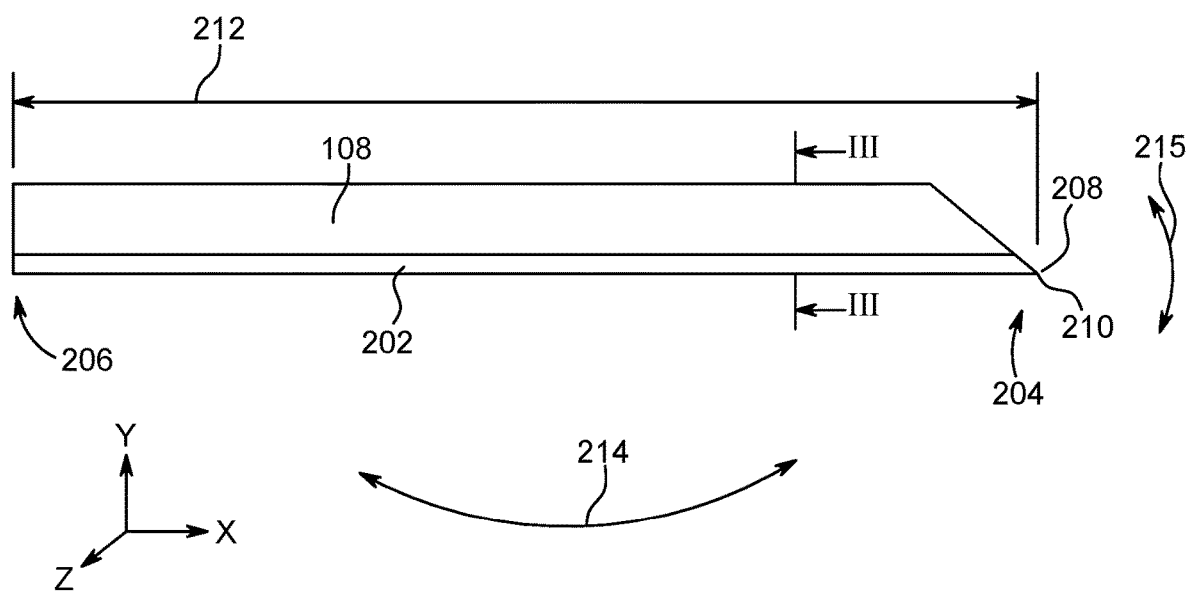
FIG. 2B is a side view of the needle of FIG. 2A.

In a preferred embodiment, the needle 100 comprises a spine body 202 formed from a rigid material, as an elongate member as illustrated in FIG. 2B. The material is rigid in the sense that it can be pressed from the tip or either end of the spine body 202 in the longitudinal direction along the axis of the spine body without deforming, yet flexible in that it can still maintain sufficient flexibility to move in other directions upon being subject to a force acting upon it, other than along the longitudinal axis of the spine body 202. Similar to object in FIG. 1, the spine body 202 in FIGS. 2A and 2B has enhanced flexibility in the plane of curve 214 (XY plane) over the plane of curve 215 (XZ plane). The enhanced flexibility characteristics may be beneficial to patient comfort when the needle is placed within the body so that the XY plane is placed in the predominant bending plane of the body. However, flexibility of the needle may occur in all planes.

In an embodiment, the spine body 202 may be formed from metal, such as stainless steel. In other embodiments, the spine body 202 may be formed from materials including but not limited to plastics, reinforced plastics, composite materials, nylon, or other materials. The spine body 202 includes a proximal end 204 that may terminate in a piercing tip 208 and a distal end 206.

Figure 3A:
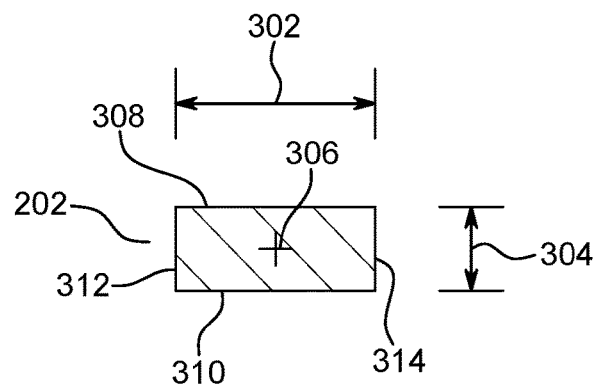
FIG. 3A is a cross-sectional view of the spine body of FIG. 2A in accordance with an embodiment taken along III-III having a rectangular cross section.

The spine body 202 has a generally rectangular cross section with a width 302 greater than the thickness 304 as illustrated in the non-limiting embodiment of FIG. 3A. The width 302 across the top surface of the spine body 202 and the length L form the bounds of a top surface 308, and the width 303 across the bottom surface of the spine body 202 and the length L form the bounds of a bottom surface 310, opposite the top surface 308. The thickness 304 and the length L form the bounds of opposite side surfaces 312 and 314 so that the side surfaces 312, 314 join the top and bottom surfaces 308, 310.

Figure 3B:
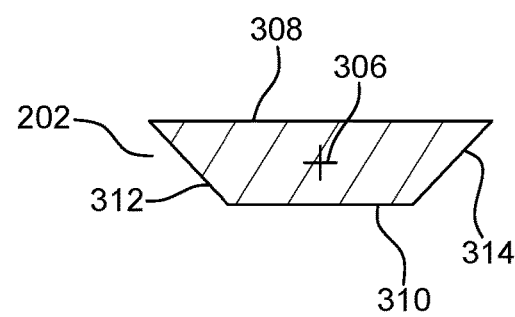
FIG. 3B is a cross sectional view of the spine body of FIG. 2A in accordance with an embodiment taken along III-III having a trapezoidal cross section.

In a non-limiting embodiment of FIG. 3B, the cross section of the spine body 202 may be a trapezoid, for example an isosceles trapezoid arranged with the width 303 of the bottom surface 310 shorter than the width 302 of the top surface 308. The thickness 304 and the length L also form the bounds of opposite side surfaces 312 and 314 so that the side surfaces 312, 314 join the top and bottom surfaces 308, 310.

Figure 3C:
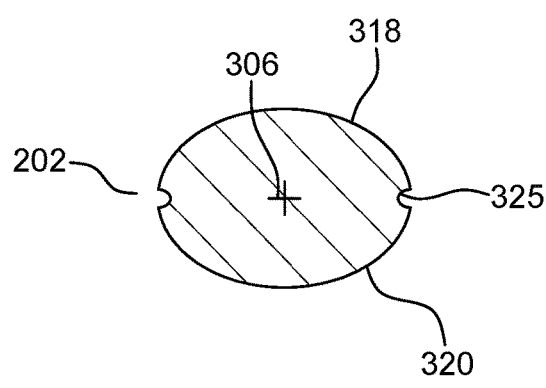
FIG. 3C is a cross sectional view of the spine body of FIG. 2A in accordance with an embodiment taken along III-III having an oval cross section.
Figure 3D:
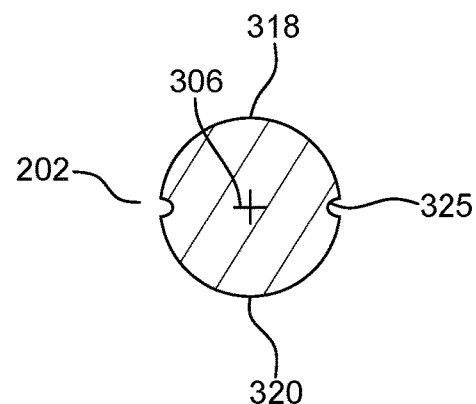
FIG. 3D is a cross sectional view of the spine body of FIG. 2A in accordance with an embodiment taken along III-III having a circular cross section.

Other embodiments of the cross-section of the spine body 202 within the scope of this disclosure include variations on the rectangular cross section shown in FIG. 3A, such as rounded or chamfered corners (not shown), a trapezoid (FIG. 3B), a compressed spherical cross section such as an elliptical (FIG. 3C), and a spherical cross section (FIG. 3D).

In some embodiments, a groove 325, configured to attach the flexible shaft portion 108 to the spine body 202, is formed in the longitudinal direction of the spine body 202 along both sides of an exterior surface. The surface of the spine body 202 above the longitudinal groove forms the bounds of a curved top surface 318 of the spine body 202, and the surface of the spine body 202 below the longitudinal groove forms the bounds of a curved bottom surface 320 of the spine body 202. This longitudinal groove is preferred in embodiments having cross-sections of the spine body 202 that are elliptical, spherical, or similar, but can also be present along the spine body 202 in embodiments having cross-sections of the spine body 202 that are generally rectangular, trapezoidal, or similar.

The piercing tip 208 may be integrally formed with the spine body 202 and transitions from a cross section corresponding with the cross sections described and illustrated for FIGS. 4A-D. of the spine body 202 to a sharp point 210. The piercing tip 208 may terminate at a point 210 formed from the convergence of the first and second surfaces 308, 310 and the side surfaces 312, 314, in the case of the generally rectangular or trapezoid cross sections of the spine body 202, or from the convergence of all surfaces, in the case of the generally spherical or elliptical cross sections of the spine body 202. In an embodiment, the piercing tip 208 may be any suitable tip including but not limited to a single-bevel, multi-bevel, multi-facet, Cournand, or other piercing tip known in the art in.

Another non-limiting embodiment of the piercing tip 208 is shown in FIGS. 4A and 4B. As illustrated, the piercing tip 208 has a beveled end 402 terminating at the sharp point 210, wherein the beveled end 402 may be formed to any suitable angle A to facilitate piercing and penetrating the tissue. The beveled end 402 may also extend above the thickness 304 of the spine body 202 forming an extended beveled portion 406. An extended beveled portion passage 408, formed from an opening in the surface of the extended beveled portion 406, is bounded by wall 410, which is illustrated as a perforated line to indicate its interior location and may be a continuous surface configured to be in fluid communication with passage 110.

In an exemplary embodiment, extended beveled portion passage 408 corresponds with passage 110, and the passages are axially aligned. This may facilitate a smoother flow through the piercing tip 208 and extended beveled portion passage 408, to passage 110. Smooth flow is understood to mean a flow unhindered by discontinuities in the wall of the passage through which the flow is established.

In an embodiment, the flow area presented in the direction of the flow would remain unchanged, or substantially unchanged. Accordingly, both passage 110 and extended beveled portion passage 408 would have a shape and dimensions that are substantially the same, with passage walls (e.g., inner surface) that align to present a smooth surface. In this case, a smooth flow would be unhindered by discontinuities between extended beveled portion passage 408 and passage 110.

In an embodiment, passage 110 and extended beveled portion passage 408 overlap in the axial direction. In another embodiment, passage 110 extends further than extended beveled portion passage 408 in the radial direction such that passage 110 may surround extended beveled portion passage 408 in the portion where the two passages overlap.

The extended bevel portion 406 includes an end 412 distal to the sharp point 210 that does not extend radially beyond the flexible shaft portion 108.

In addition to multiple embodiments representing the piercing tip 208, there exist multiple embodiments of the flexible shaft portion 108. In an embodiment, the proximal end of the flexible shaft portion 108 may be perpendicular to an axis along the length L of the spine body 202, as illustrated in FIG. 4A. FIG. 4C represents a top view of the piercing tip illustrated in FIG. 4A, which demonstrates that the proximal end 414 of the flexible shaft portion 108 does not have a beveled surface having an angle A that corresponds to the extended beveled portion 406 of the spine body 202. As such, the opening that can be seen from this view includes passage 408, formed through the opening of the piercing tip 208 only. The opening to passage 110, formed through the opening of the shaft, cannot be observed from this top view.

In an exemplary embodiment, the proximal end of the flexible shaft portion 108 may include a beveled end portion, as illustrated in FIG. 4B. The surface of the beveled end portion may run along with or parallel to the extended beveled portion 406 of the piercing tip 208 at a same angle A. In an exemplary embodiment, the surface of the beveled end portion is parallel to and located interiorly from the extended beveled portion 406 of the piercing tip 208. Having a beveled end on the flexible portion may allow for easier insertion of the needle into the material that it is penetrating. For example, if the piercing tip of the spine body breaks a skin surface, there will eventually be a transition from the more rigid material of the spine body to the more flexible material of the flexible portion as the needle is further inserted. If this transition is more gradual, for example when the end of the flexible portion is beveled as well, then there may be less stress acting upon both the needle and the material that it is penetrating.

FIG. 4D represents a top view of the piercing tip illustrated in FIG. 4B, which demonstrates that the proximal end 414 of the flexible portion does have a beveled surface, the beveled end portion, having an angle A that corresponds to the extended beveled portion 406 of the spine body 202. As such, the opening that can be seen from this view may include passage 110, formed through the opening of the shaft, and extended beveled portion passage 408, formed through the opening of the piercing tip 208.

Returning to FIG. 2A, the flexible shaft portion 108 is formed along at least part of the length L of the elongate spine 202 forming a needle shaft 112 having a passage 110 formed therein. In a preferred embodiment, passage 110 extends for the length L of the needle 100. In other embodiments, passage 110 may extend partially along the length L. In some, embodiments, passage 110 may be in fluid communication with another passage (not shown) through a wall of the needle 100.

As illustrated in FIGS. 5A-5D, which represents sectional views of various embodiments of the needle of FIG. 2A taken along line V-V wherein the cross section of the spine body is rectangular as shown in FIG. 3A, passage 110 may be bounded by a portion of an inner surface 502 of the flexible shaft portion 108. An outer surface 504, generally parallel to the inner surface 502, and the inner surface 502 define the wall thickness T. The wall thickness T may be uniform (as illustrated for simplicity) or may vary at different locations of the flexible shaft portion 108.

Figure 5A:
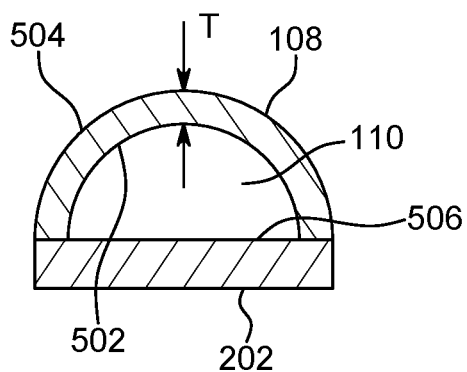
FIGS. 5A-5F are sectional views of various embodiments of the needle of FIG. 2A taken along line V-V.

Passage 110 may also be bounded by a portion of a top surface, for example surface 506 of the spine body 202. The surface 506 may be bounded by a portion of the width 302 of the spine body 202 (as illustrated in FIG. 5A) and at least some of the length 212 of the spine body 202. In another embodiment, the surface 506 may be bounded by all of the width 302 of the spine body 202 (as illustrated in FIG. 5B) and at least some of the length 212 of the spine body 202.

Figure 5B:
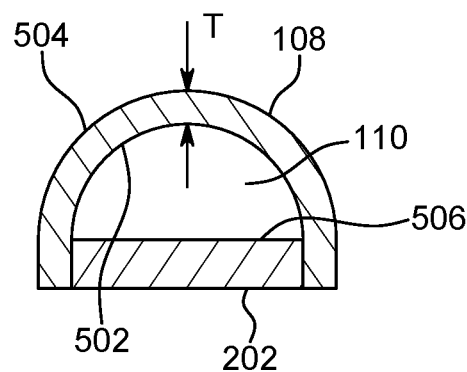
Figure 5C:
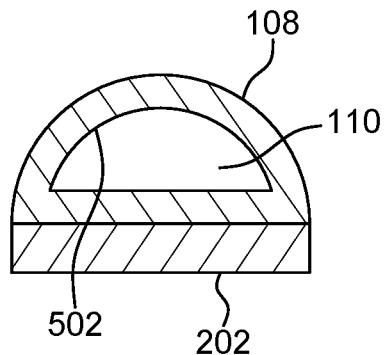
Figure 5D:
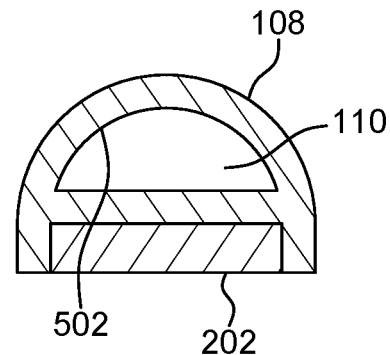

In other embodiments illustrated in FIGS. 5C and 5D, passage 110 may be bounded entirely by the inner surface 502 of the flexible shaft portion 108.

In the non-limiting embodiments of FIGS. 5A-5D, the cross-sectional shape of the elongate spine is rectangular. Other cross-sectional shapes may be used with similar beneficial results. For example, in another embodiment, wherein the cross section of the elongate spine is trapezoidal, as shown in FIG. 3B, passage 110 may also be bounded by an inner surface 502 of the flexible shaft portion 108. Passage 110 may also be bounded by a portion of a top surface, for example surface 506 of the spine body 202. The surface 506 may itself be bounded by a portion of the width 302 of the spine body 202 (as illustrated in FIG. 5A) and at least some of the length 212 of the spine body 202. In another embodiment, the surface 506 may be bounded by all of the width 302 of the spine body 202 (as illustrated in FIG. 5B) and at least some of the length 212 of the spine body 202.

In other embodiments, passage 110 may be bounded entirely by the inner surface 502 of the flexible shaft portion 108.

In the non-limiting embodiments of FIGS. 5A-5D, passage 110 is illustrated to be substantially semi-circular in cross section for ease of illustration only. Other shapes may be used with similar beneficial results.

Figure 5E:
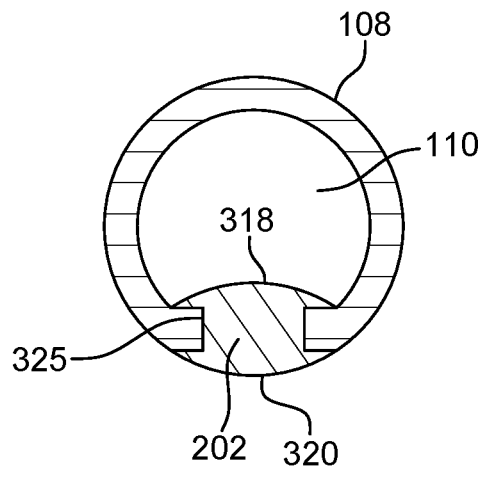
Figure 5F:
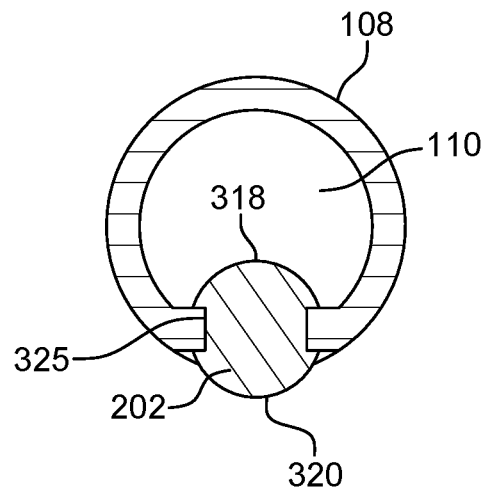

In other embodiments, the cross section of the spine body 202 may be elliptical, as shown in FIG. 3C, or spherical as shown in FIG. 3D. In at least each of these instances the flexible shaft portion 108 may attach to a surface of the spine body 202 at a groove 325, which is located along a portion of the length of the spine body 202, and is configured for attachment of the flexible shaft portion 108 as illustrated in FIGS. 5E-5F. In these embodiments, passage 110 is bound by a curved top surface 318 of the spine body 202 and a portion of the inner surface of the flexible shaft portion 108, wherein the curved top surface 318 may refer to surface portions that are above the longitudinal groove 325 and a curved bottom surface 320 may refer to surface portions that are below the longitudinal groove 325. In these embodiments, passage 110 may still be substantially semicircular. Attachment of the flexible portion 110 to a surface of the spine body 202 wherein a longitudinal groove 325 is located can also occur for embodiments having a cross section of the spine body that is trapezoidal or rectangular as illustrated in FIGS. 3A-3B.

In the embodiments of FIGS. 5A-5F, portions of the flexible shaft portion 108 are disposed on portions of the spine body 202. In a preferred embodiment, the flexible shaft portion 108 is formed in a molding operation onto portions of the spine body 202, for example in an insert molding operation. In other embodiments, the flexible portion may be formed in a molding operation separately from the spine body 202 and combined with the spine body 202 using bonding techniques, such as mechanical bonding, adhesive bonding, ultrasonic bonding, heat bonding, or ultraviolet (UV) bonding, wherein an adhesive material is activated by UV rays.

In some embodiments, the portions of the spine body 202 onto which the flexible shaft portion 108 will be disposed are formed with details to facilitate the attachment of the flexible shaft portion 108. For example, the prescribed portions of the spine body 202 may include surface texturing or treatment, or physical features, such as undercuts, that may enhance the attachment of the flexible shaft portion 108 to the spine body 202.

Figure 6A:
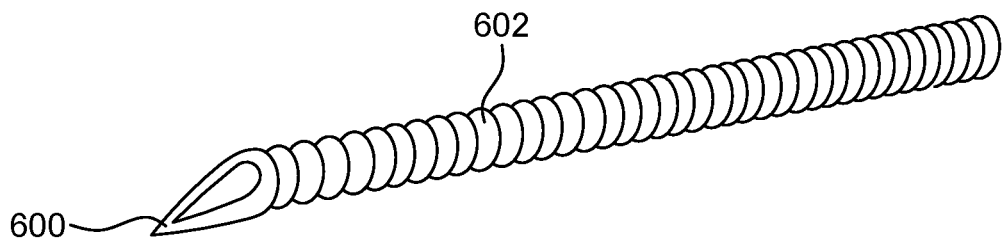
FIG. 6A is a perspective view of a spine body that is coiled.
Figure 6B:
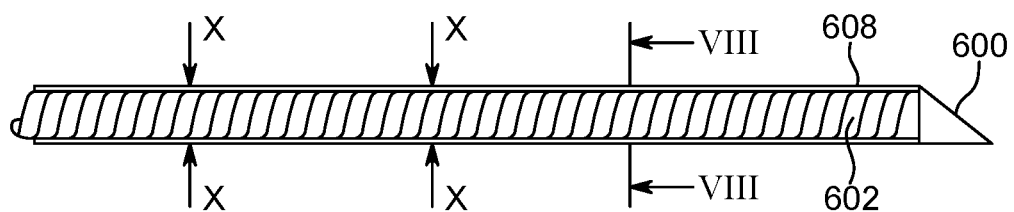
FIG. 6B is a side view of the coiled-spine body of FIG. 6A having a flexible coat surrounding the exterior surface.
Figure 6C:
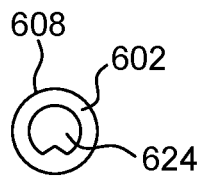
FIG. 6C is a cross-sectional view of the coiled-spine body of FIG. 6B, having a flexible coat surrounding the exterior surface, taken along line VIII-VIII.
Figure 6D:
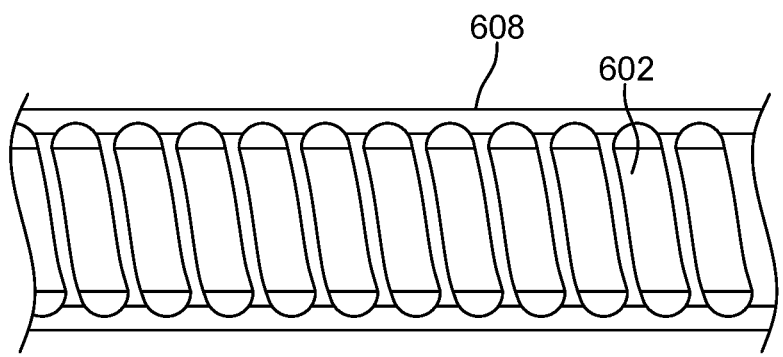
FIG. 6D is a cross-sectional view of the coiled-spine body of FIG. 6B, having a flexible coat surrounding the exterior surface, taken along line X-X in the longitudinal direction.

In an alternative embodiment illustrated in FIGS. 6A-6D, the spine body is a coiled spine body 602 having its own axial passage 624. In some embodiments, the flexible shaft portion 608 may surround the exterior surface of the coiled-spine body 602, such that the coiled-spine body 602 defines the axial passage 624 and is itself surrounded by the flexible shaft portion 608 as illustrated in FIGS. 6B-6D. In an embodiment, the exterior surface of the flexible shaft portion 608 may also help facilitate a smooth flow from the piercing tip 600 to the axial passage 624.

FIG. 6C is a cross-section of the coiled-spine body 602 of FIG. 6B taken along line VIII-VIII illustrating the axial passage 624 formed and surrounded by the coiled spine body 602, and an exterior surface, which represents the flexible shaft portion 608. FIG. 6D is a cross-section of the coiled-spine body 602 of FIG. 6B taken along lines X-X in the longitudinal direction from a segment of the needle apparatus.

The flexible shaft portion 608 could be formed from any flexible material. Non-limiting examples of the flexible material may include Teflon, silicon, polytetrafluoroethylene-based polymers, a thermoplastic elastomer (TPE), or other polymeric material having a low durometer. In an embodiment, the flexible material is biocompatible, although non-biocompatible materials may be used, for example if bio-compatibility is not required. In an embodiment, the flexible material is a polymer, although non-polymeric materials may be used if the material is flexible. In a preferred embodiment, the polymer used to form the flexible portion has a lubricity characteristic to facilitate insertion of the needle 100. The lubricity may be a feature of the flexible material itself, or that of an additive to the material or a coating applied to the external surfaces of the flexible portion 608. In an embodiment the flexible material could be any material that could stretch.

In an embodiment, the coiled-spine body 602 may be formed from a metal, such as stainless steel. In other embodiments, the coiled-spine body 602 may be formed from other materials, including but not limited to plastics, reinforced plastics, composite materials, nylon, or other materials.

In an embodiment, the material used to form the coiled spine body 602 is such that it can be pressed from the tip or either end of the coiled spine body 602 in the longitudinal direction along the axis of the spine body without deforming, yet flexible in that it can still maintain sufficient flexibility to move in other directions upon being subject to a force acting upon it, other than along the longitudinal axis of the coiled spine body 602.

In an embodiment, the coils of the coiled spine body 602 could be spaced apart. In another embodiment, the coils of the coiled spine body 602 have no gaps between them, which may avoid compression of the coiled spine body 602. The internal structure of the coiled-spine body 602 may be bendable.

In an embodiment, the piercing tip 600 may be integrally formed with the coiled-spine body 602. The piercing tip 600 may be any suitable tip including but not limited to a single-bevel, multi-bevel, multi-facet, Cournand, or other piercing tips known in the art.

In an exemplary embodiment, the piercing tip 600 may have a beveled end or extended beveled portion similar to the beveled end 402 or extended beveled portion 406 described for FIGS. 4A and 4B, terminating at a sharp point. In this embodiment, an opening in the surface of the extended beveled portion would be present and may align with the opening to the axial passage 624 of the coiled spine body 602. Alignment of these openings may help to facilitate smooth flow through the piercing tip 600 and the axial passage 624. The extended beveled portion equivalent of the piercing tip 600 may be formed to any suitable angle to facilitate piercing and penetrating the tissue.

In an embodiment, the proximal end of the flexible shaft portion 608 is approximately perpendicular to an axis along the length of the spine body 602, similar to the flexible shaft portion 108 described for FIG. 4A.

In an exemplary embodiment, the proximal end of the flexible shaft portion 608 may include a beveled end portion, similar to the beveled end portion of the flexible shaft portion 108 described for FIG. 4B. The surface of the beveled end portion equivalent of the flexible shaft portion 608 may be coplanar with the extended beveled portion equivalent of the piercing tip 600 at a same angle A. In an exemplary embodiment, the surface of the beveled end portion equivalent is parallel to and located interiorly from the extended beveled portion equivalent of the piercing tip 600.

In an embodiment, the coiled spine body 602 may extend beyond the proximal end of the flexible shaft portion 608 as illustrated in FIG. 4B. In another embodiment, the opening of the axial passage 624 may also extend beyond the proximal end of the flexible shaft portion 608.

In an embodiment, the proximal end of the flexible shaft portion 608 includes a beveled end portion equivalent coplanar with the beveled end equivalent of the piercing tip 600. In this embodiment, an opening in the surface of the beveled end portion equivalent of the flexible shaft portion 608 may align axially with the opening to the axial passage 624 of the coiled spine body 602. Alignment of these openings may help to facilitate smooth flow through the piercing tip and the axial passage 624.

The needle, as described in the foregoing, has been observed to have features not found in other known medical needles. Beneficially, embodiments of the needle have sufficient stiffness in compression to pierce the skin and penetrate flesh below the skin as required. However, embodiments have sufficient flexibility to provide patient comfort while the needle is indwelling, i.e., remains in the patient for a period of time, without immobilization of the body part containing the needle. For example, in a venipuncture application, the disclosed needle can remain in an ambulatory recipient, virtually discomfort-free, without fewer limitations to movement than current needle systems.

It is understood that a contributing factor to the beneficial features of the disclosed needle is the configuration of the spine body 202. As designed, the spine body 202 provides rigidity in axial compression (i.e., in the direction of the longitudinal axis 306, FIG. 2A), which may beneficially influence the ease of piercing the skin and tissue with the needle 100. As designed, the spine body 202 also provides enhanced flexibility, especially in the direction of the smaller dimension. For example, the spine body 202 of FIG. 2B may have enhanced flexibility in the plane of curve 214 (XY plane) over the plane of curve 215 (XZ plane). The enhanced flexibility characteristics may be beneficial to patient comfort when the needle is placed within the body so that the XY plane is placed in the predominant bending plane of the body.

It is also generally understood that an element with different shaped cross-sections, such as those represented in FIGS. 3B-3D, or those that are elliptical in nature, would have enhanced flexibility in certain directions and may not be limited to enhanced flexibility in one plane only.

What is claimed is:

1. A flexible medical needle apparatus comprising:
    a spine body comprising a first end, a second end, a length, and a cross section, wherein the cross section of the spine body is generally elliptical or spherical, comprising a curved top surface, a curved bottom surface, and a longitudinal groove;
    a piercing tip, wherein the piercing tip is connected to the spine body at the first end; and
    a flexible shaft portion comprising a proximal end and a distal end, wherein
    the flexible shaft portion is disposed on at least a portion of the spine body forming a needle shaft,
    the proximal end of the flexible shaft portion includes an opening and is adjacent to the first end of the spine body,
    the distal end of the flexible shaft portion is adjacent to the second end of the spine body, and
    the needle shaft comprises a passage having an inner surface,
    the longitudinal groove extends along at least a portion of the length of the spine body having the cross section that is generally elliptical or spherical, and is configured to attach the flexible shaft portion to the spine body,
    the curved top surface is located above the longitudinal groove and the curved bottom surface is located below the longitudinal groove, and
    the passage is bounded by the curved top surface of the spine body and the inner surface of the flexible shaft portion that extends until attachment with the longitudinal groove.

2. The flexible medical needle apparatus of claim 1, wherein the flexible shaft portion is formed from at least one of a flexible material, a polymeric material having a low durometer, polytetrafluoroethylene-based polymers, silicon, Teflon, or a thermoplastic elastomer.

3. The flexible medical needle apparatus of claim 1, wherein the piercing tip terminates at a point comprising convergence of all surfaces of the spine body.

4. The flexible medical needle apparatus of claim 1, wherein the piercing tip includes a beveled end.

5. The flexible medical needle apparatus of claim 1, wherein the piercing tip includes an extended beveled portion comprising a continuous surface and comprising an extended beveled opening.

6. The flexible medical needle apparatus of claim 1, wherein the opening of the proximal end of the flexible shaft portion is perpendicular to an axis along the length of the spine body.

7. The apparatus of claim 1, wherein the opening of the proximal end of the flexible shaft portion includes a beveled end portion.

8. The flexible medical needle apparatus of claim 1, wherein a material used to form the flexible shaft portion has a lubricity characteristic to facilitate insertion of the flexible medical needle apparatus.

* * * * *